US010242489B2

(12) United States Patent
Yoshida et al.

(10) Patent No.: US 10,242,489 B2
(45) Date of Patent: Mar. 26, 2019

(54) IMAGE PROCESSING DEVICE, IMAGE PROCESSING METHOD AND IMAGE PROCESSING SYSTEM

(71) Applicant: Hitachi, Ltd., Tokyo (JP)

(72) Inventors: Hanae Yoshida, Tokyo (JP); Maki Tanaka, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 114 days.

(21) Appl. No.: 15/316,548

(22) PCT Filed: Jun. 5, 2015

(86) PCT No.: PCT/JP2015/066338
§ 371 (c)(1),
(2) Date: Dec. 6, 2016

(87) PCT Pub. No.: WO2015/198835
PCT Pub. Date: Dec. 30, 2015

(65) Prior Publication Data
US 2017/0243391 A1 Aug. 24, 2017

(30) Foreign Application Priority Data
Jun. 26, 2014 (JP) ................................ 2014-131587

(51) Int. Cl.
*G06T 15/20* (2011.01)
*G06T 15/08* (2011.01)
(Continued)

(52) U.S. Cl.
CPC .............. *G06T 15/08* (2013.01); *A61B 5/055* (2013.01); *A61B 6/03* (2013.01); *A61B 8/469* (2013.01);
(Continued)

(58) Field of Classification Search
CPC ........... G06F 15/08; A61B 6/03; A61B 5/055; A61B 8/469; A61B 8/483; A61B 8/523; G06T 15/20
See application file for complete search history.

(56) References Cited

U.S. PATENT DOCUMENTS

2004/0106869 A1\* 6/2004 Tepper ................. A61B 8/0833
600/443
2006/0274065 A1\* 12/2006 Buyanovskiy .......... G06T 15/06
345/424
(Continued)

FOREIGN PATENT DOCUMENTS

JP 08-166995 A 6/1996
JP 2000-000235 A 1/2000
(Continued)

OTHER PUBLICATIONS

International Search Report of PCT/JP2015/066338 dated Aug. 25, 2015.

*Primary Examiner* — Robert J Craddock
(74) *Attorney, Agent, or Firm* — Mattingly & Malur, PC

(57) ABSTRACT

An image processing device and an image processing method that performs image interpretation as fast as possible, without oversight by an interactive operation, when performing the image interpretation of a large amount of volume data in which an interest region is set in advance are provided. The image processing device that generates a two-dimensional image from a captured three-dimensional image and displays the generated two-dimensional image receives an input signal relating to primary display control information including a speed of a display control input of the two-dimensional image, calculates the primary display control information from the input signal, calculates secondary display control information including a display speed of the two-dimensional image based on information of an interest region and the primary display control information, (Continued)

and sequentially generates the two-dimensional images based on the secondary display control information and displays the generated two-dimensional image.

14 Claims, 11 Drawing Sheets

(51) Int. Cl.
*A61B 6/03* (2006.01)
*A61B 5/055* (2006.01)
*A61B 8/00* (2006.01)
*A61B 8/08* (2006.01)

(52) U.S. Cl.
CPC .............. *A61B 8/483* (2013.01); *A61B 8/523* (2013.01); *G06T 15/20* (2013.01); *A61B 2576/00* (2013.01); *G06T 2210/41* (2013.01)

(56) References Cited

U.S. PATENT DOCUMENTS

2010/0026781 A1* 2/2010 Ali ..................... G06K 9/00234
 348/14.08
2015/0164450 A1* 6/2015 Kotlapalli .............. A61B 6/481
 600/431

FOREIGN PATENT DOCUMENTS

JP 2000-262517 A 9/2000
JP 2013-085622 A 5/2013

* cited by examiner

F I G. 3

| INPUT | i[0] | i[1] | i[2] | i[3] | i[4] | i[5] | i[6] | i[7] | i[8] | i[9] | i[10] |
|---|---|---|---|---|---|---|---|---|---|---|---|
| INPUT TIME | t[0] | t[1] | t[2] | t[3] | t[4] | t[5] | t[6] | t[7] | t[8] | t[9] | t[10] |
| INPUT SPEED |  | v[1] | v[2] | v[3] | v[4] | v[5] | v[6] | v[7] | v[8] | v[9] | v[10] |
| CONTINUOUS INPUT NUMBER | – | – | – | – | – | ni[1] | – | – | – | – | ni[2] |
| CONTINUOUS SPEED | – | – | – | – | vc[1] | – | – | – | – | vc[2] | – |
| BLANK SPEED | – | – | – | – | – | vb[1] | – | – | – | – | vb[2] |
| SERIES SPEED | – | – | – | – | – | va[1] | – | – | – | – | va[2] |

TIME →

F I G. 5

<EXAMPLE OF INTEREST DEGREE SETTING TABLE>

|  |  | DEGREE OF INTEREST |
|---|---|---|
| SECTION POSITION | EQUAL TO OR GREATER THAN s_0 AND LESS THAN s_r0 | d_a |
|  | EQUAL TO OR GREATER THAN s_r0 AND LESS THAN s_r1 | d_b |
|  | EQUAL TO OR GREATER THAN s_r1 AND EQUAL TO OR LESS THAN s_e | d_a | d_b>d_a

FIG. 6

<EXAMPLE OF TIME INTERVAL SETTING TABLE>

CASE OF CHANGE FLAG $f < f\_th$

|  |  | INPUT SPEED | |
|---|---|---|---|
|  |  | LESS THAN $v\_th$ | EQUAL TO OR GREATER THAN $v\_th$ |
| DEGREE OF INTEREST | $d\_a$ | $ti\_a$ | $ti\_a$ |
|  | $d\_b$ | $ti\_a$ | $ti\_b$ |

CASE OF CHANGE FLAG $f \geq f\_th$

|  |  | INPUT SPEED | |
|---|---|---|---|
|  |  | LESS THAN $v\_th$ | EQUAL TO OR GREATER THAN $v\_th$ |
| DEGREE OF INTEREST | $d\_a$ | $ti\_a$ | $ti\_a$ |
|  | $d\_b$ | $ti\_a$ | $ti\_a$ |

$ti\_b > ti\_a$

F I G. 7

| INPUT | INPUT TIME | INPUT SPEED | DEGREE OF INTEREST | TIME INTERVAL |
|---|---|---|---|---|
| i[0] | t[0] | v[0] | d[0]=d_a | ti[0]=ti_a |
| i[1] | t[1] | v[1] | d[1]=d_a | ti[1]=ti_a |
| i[2] | t[2] | v[2] | d[2]=d_b | ti[2]=ti_b |
| i[3] | t[3] | v[3] | d[3]=d_b | ti[3]=ti_a |
| i[4] | t[4] | v[4] | d[4]=d_b | ti[4]=ti_a |
| i[5] | t[5] | v[5] | d[5]=d_a | ti[5]=ti_a |

$v[0], v[1], v[2], \geq v\_th$

CASE OF $v[3] < v\_th$

FIG. 9

<EXAMPLE OF SECTION INTERVAL SETTING TABLE>

CASE OF CHANGE FLAG $f < f\_th$

|  |  | INPUT SPEED | |
| --- | --- | --- | --- |
|  |  | LESS THAN $v\_th$ | EQUAL TO OR GREATER THAN $v\_th$ |
| DEGREE OF INTEREST | $d\_a$ | $g\_a$ | $g\_a$ |
|  | $d\_b$ | $g\_a$ | $g\_b$ |

CASE OF CHANGE FLAG $f \geq f\_th$

|  |  | INPUT SPEED | |
| --- | --- | --- | --- |
|  |  | LESS THAN $v\_th$ | EQUAL TO OR GREATER THAN $v\_th$ |
| DEGREE OF INTEREST | $d\_a$ | $g\_a$ | $g\_a$ |
|  | $d\_b$ | $g\_a$ | $g\_a$ |

$g\_a > g\_b$

<EXAMPLE OF INTEREST DEGREE SETTING TABLE>

| | | DEGREE OF INTEREST |
|---|---|---|
| VIEWPOINT ANGLE | EQUAL TO OR GREATER THAN a_0 AND LESS THAN a_r0 | d_0 |
| | EQUAL TO OR GREATER THAN a_r0 AND LESS THAN a_r1 | d_1 |
| | EQUAL TO OR GREATER THAN a_r1 AND EQUAL TO OR LESS THAN a_e | d_0 |

F I G. 1 2

<EXAMPLE OF INTEREST DEGREE SETTING TABLE>

| x | y | z | RADIUS | DEGREE OF INTEREST |
|---|---|---|---|---|
| x_r0 | y_r0 | z_r0 | r_r0 | d_0 |
| x_r1 | y_r1 | z_r1 | r_r1 | d_1 |
| x_r2 | y_r2 | z_r2 | r_r2 | d_2 |
| POSITION NOT CORRESPONDING TO ABOVE | | | | d_3 |

IMAGE PROCESSING DEVICE, IMAGE PROCESSING METHOD AND IMAGE PROCESSING SYSTEM

TECHNICAL FIELD

The present invention relates to an image processing device and an image processing method for generating a two-dimensional image from a three-dimensional image and displaying the image.

BACKGROUND ART

In a diagnosis in which a medical image inspection apparatus represented by an X-ray computed tomography (X-ray CT) apparatus, a magnetic resonance imaging (MRI) apparatus or the like is used, it is common that a captured three-dimensional medical image (hereinafter also referred to as "volume data") is reconstructed as a continuous two-dimensional image and then image interpretation is performed.

There is a trend of imaging apparatuses becoming more sophisticated every year and the data size per volume data tending to increase. In addition, especially in a CT apparatus, imaging of high-quality volume data using low doses has become possible and imaging opportunities have also tended to increase. Therefore, a burden on a doctor or an engineer who performs the image interpretation for this large amount of medical volume data is very high.

In order to mitigate the burden, there is growing a need for the use of computer aided detection, or computer aided diagnosis (CAD). CAD refers to a system and a technique which perform quantification and analysis of image information with a computer and an information processing technique based on a computer.

A typical function of CAD includes a function which automatically extracts a high suspicion disease region using an image processing technology from values and a distribution of voxels of the medical volume data as target data and then provides the high suspicion disease region as an interest region, for example. However, CAD performs only support regarding the diagnosis and thus confirmation of a doctor is required upon the diagnosis including determination of whether or not the interest region falls on a disease region.

In a case of performing the image interpretation of the volume data in which the interest region is set in advance by the CAD or the like, as matters required of a doctor or an engineer to confirm, there are confirmation whether or not the interest region is correctly set to the disease region while looking at the interest region set in advance and confirmation whether or not there is no disease region while looking at the area where the interest region has not been set. It is necessary to confirm the regions without oversights, as fast as possible.

In the related art, when performing the image interpretation of a large amount of volume data in which the interest region is set in advance, a technique of performing the interpretation without oversights, as fast as possible has been proposed.

For example, in PTL 1, an apparatus and a program which allow in-depth image interpretation by delaying a display speed of the image data generated in an image section intersecting with the interest region than a display speed of the image data generated in other image sections are proposed.

CITATION LIST

Patent Literature

PTL 1: JP-A-2013-85622

SUMMARY OF INVENTION

Technical Problem

In the technique disclosed in PTL 1, there is a problem that, during the image interpretation, since a display speed automatically decreases to a delayed speed, a portion which is considered to be unnecessary by an operator is also displayed at a low speed and as a result, the entire image interpretation time is increased, and since the image interpretation is an operation of which interactivity is low, stress of the operator increases.

An object of the present invention is to provide an image processing device and an image processing method which can perform image interpretation with less oversight, as fast as possible, by an interactive operation.

Solution to Problem

An image processing device according to the present invention includes a storage unit that stores an image database relating to a three-dimensional image; an input receiving unit that receives an input signal according to an operation of a user terminal; a primary display control information calculating unit that calculates primary display control information including a speed of the received input signal; a secondary display control information calculating unit that calculates secondary display control information including a display speed of a two-dimensional image which is generated from the three-dimensional image based on information of an interest region determined as a high suspicion disease region in the three-dimensional image and the calculated primary display control information; and an image generation and transmission unit that sequentially generates the two-dimensional images and transmits the generated two-dimensional image to the user terminal, based on the calculated secondary display control information.

Advantageous Effects of Invention

According to the present invention, image interpretation can be performed as fast as possible, with less oversight by an interactive operation of an input unit.

BRIEF DESCRIPTION OF DRAWINGS

FIG. 3 is a view illustrating an example of a process calculating an input speed from input.

FIG. 5 is a view illustrating an interest degree setting table in which the degree of interest with respect to section positions is set, according to Example 2.

FIG. 6 is a view illustrating a time interval setting table in which time intervals between input times and display times are set.

FIG. 7 is a view illustrating relationships between the degrees of interest when crossing interest regions and the time intervals from input to display.

FIG. 9 is a view illustrating a section interval setting table in which section intervals are set with respect to change flags displaying the degree of interest of the interest regions, the input speeds and a history thereof, according to Example 3.

FIG. 12 is a view illustrating the interest degree setting table in which the degree of interest with respect to a three-dimensional position of the volume data is set.

DESCRIPTION OF EMBODIMENTS

Hereinafter, four examples will be described using the drawings.

EXAMPLE 1

In the present example, an example of an image processing device determining secondary display control information according to primary display control information will be described. Here, the primary display control information is a speed of a pulse input signal detecting wheel rotation of a mouse during image interpretation by scrolling a two-dimensional image, for example and is intermediately generated information which is a basis for calculating the secondary display control information for finally displaying the two-dimensional image on a display unit or a display device. The information will be described below in detail.

In addition, the secondary display control information is a time interval (display delay time) from an input time of the input signal to a two-dimensional image display time, for example. The information will be described below in detail.

Figure 1:
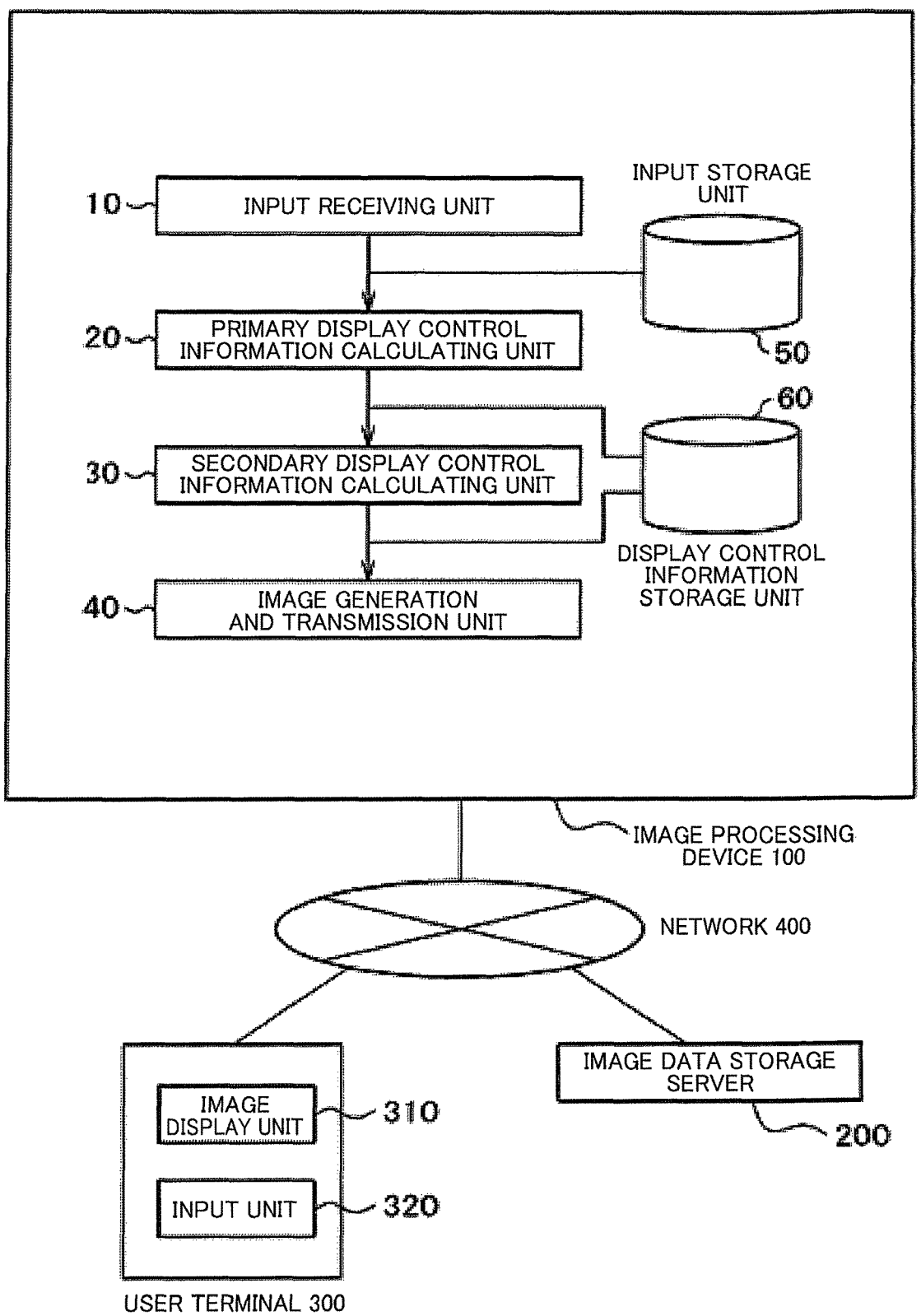
FIG. 1 is a view illustrating a configuration of an image processing system according to Example 1.

FIG. 1 is a view illustrating a configuration of an image processing system according to the present example. As illustrated in FIG. 1, the present system includes an image processing device 100 which generates the two-dimensional image by performing image processing with respect to a three-dimensional image, an image data storage server 200 which stores interest region information such as an imaged and reconstructed three-dimensional image and a position of an interest region using an X-ray CT apparatus, an MRI apparatus, or the like, a user terminal 300 which includes an input unit 320 inputting a processing request to the image processing device 100 and an image display unit 310 performing display of image data, and a network 400 which connects the image processing device 100, the image data storage server 200, and the user terminal 300 with each other.

The image processing device 100 includes an input receiving unit 10 which receives a start signal from the user terminal 300, and an input signal according to, for example, operation of movement and wheel rotation of a mouse in the input unit 320 of the user terminal 300, a primary display control information calculating unit 20 which calculates the primary display control information, a secondary display control information calculating unit 30 which calculates the secondary display control information, an image generation and transmission unit 40 which generates the two-dimensional image and transmits the generated two-dimensional image to the image display unit 310 of the user terminal 300, an input storage unit 50 which stores the input signal from the input receiving unit 10, and a display control information storage unit 60 which stores the primary display control information and the secondary display control information.

Here, the primary display control information calculating unit 20 calculates the primary display control information such as an input speed, for example, from the input signal obtained from the input receiving unit 10. In addition, the secondary display control information calculating unit 30 calculates the secondary display control information such as a display speed, for example, from the primary display control information obtained from the primary display control information calculating unit 20 and the information of the interest region and the three-dimensional image obtained from the image data storage server 200.

Figure 2:
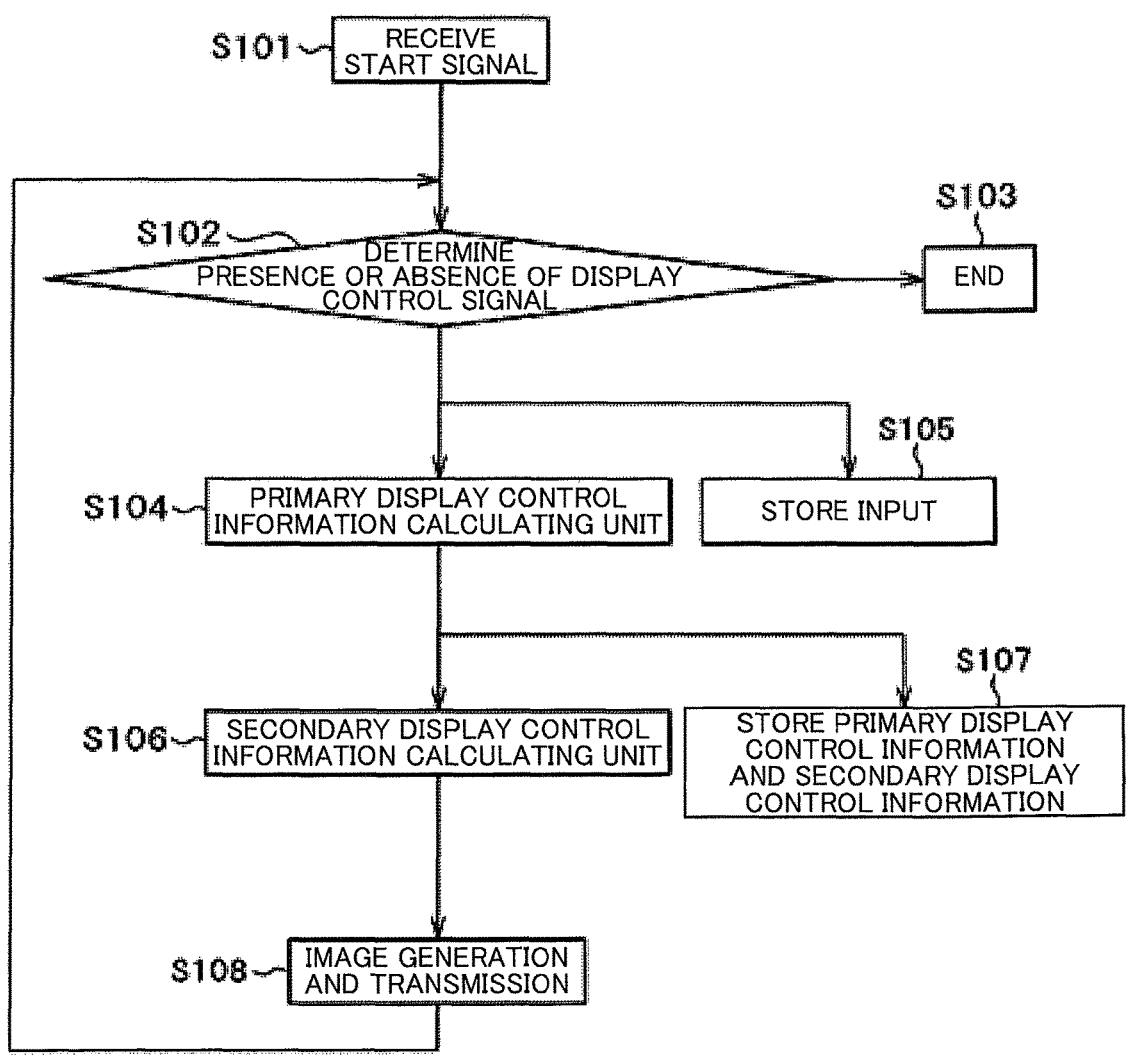
FIG. 2 is a flow chart illustrating an example of calculation process of display control information.

Next, using FIG. 2, a flow of processing when the secondary display control information is determined corresponding to the primary display control information is explained.

The input receiving unit 10 of the image processing device 100 starts image processing by receiving the start signal as an input from the input unit 320 of the user terminal 300 (S101). The input receiving unit 10 confirms the presence or the absence of the input from the input unit 320 of the user terminal 300 (S102). In a case where there is no input, the processing is terminated (S103).

In a case where there is the input, the primary display control information such as the input speed, for example, is calculated from a current input obtained from the input receiving unit 10 and input history obtained from the input storage unit 50 in the primary display control information calculating unit 20 (S104), and current input information is stored in the input storage unit 50 (S105).

Next, the secondary display control information including the display speed is calculated from history of the primary display control information obtained from the primary display control information calculating unit 20, the information of the volume data (three-dimensional medical image) and the information of the interest region obtained from the image data storage server 200, and the secondary display control information including a section position of a two-dimensional section image obtained from the display control information storage unit 60 in the secondary display control information calculating unit 30 (S106). A current primary display control information and a current secondary display control information are stored in the display control information storage unit 60 (S107).

Finally, a display image is generated or is acquired from the three-dimensional image or a plurality of two-dimensional images stored in the image data storage server 200, using the secondary display control information including the display speed and a section position of the two-dimensional section image obtained from the secondary display control information calculating unit 30 in the image generation and transmission unit 40. The two-dimensional image displayed by a determined display speed is transmitted to the image display unit 310 of the user terminal 300 (S108) and then the processing returns to S102 to repeat the same processing.

In addition, execution after the second time of S102 is not necessary to be held until the end of S108 and if only S105 is terminated, the next flow from S102 may be started. Here, a case where the input receiving unit 10 receives the input according to a screen scrolling operation of the continuous two-dimensional images, as continuous inputs will be described.

In order to describe the continuous inputs, it is considered a case where the input receiving unit 10 receives a plurality of inputs in an order of i[0], i[1], i[2], . . . Here, the inputs i[0], i[1], i[2], . . . are inputs from the input unit of the same user terminal and thus are different from each other only in an input time. Here, a case where a state of the input time difference between i[0] and i[1] and the input time difference between i[1] and i[2] being less than d_th is continued, i[0], i[1], i[2], . . . are determined as the continuous inputs and if the input time of the input received by the input receiving unit 10 is a time elapsed by d_th or more from the input time of the input received previously, it is determined that the continuous inputs are terminated.

Here, for example, in the input unit 320 of the user terminal 300, in a case where the wheel of the mouse is rotated or a curser movement is performed on the screen using the mouse, or a case where an operation by tracing with a finger or the like is performed using a touch panel, a diameter of the wheel or the screen size of the touch panel or display is limited and there is a limit of resolution of the input and even if the continuous inputs are performed, the continuous inputs are interrupted at regular interval. Even in such a case, the interruption of the input can be dealt by setting d_th larger in the above example.

Here, an example of calculating the primary display control information at S104 in a case where the input is received as the continuous inputs will be described. Usually, the speed of the continuous inputs can be considered to be equivalent to an image display speed which is desired at the operation point in time by a user, since the two-dimensional image display is performed according to the input such as the wheel rotation of the mouse. Here, it is described that the input time of the input is used and the primary display control input information is a speed of the continuous inputs. For example, in a case where the input time of input i[n] at certain point in time is t[n], in the primary display control information calculating unit 20, the input time t[n−1] of the previous input i[n−1] is used, the input speed v[n]=1/(t[n]−t[n−1]) is calculated and then it is output as the primary display control information corresponding to i[n].

Next, using FIG. 3, a case where the input receiving unit 10 receives intermittent continuous inputs will be described. FIG. 3 illustrates relationships between the input times t[0], t[1], . . . corresponding to the inputs i[0], i[1], . . . and the input speeds. Here, each of the input speeds v[1], v[2], . . . is respectively calculated as v[1]=1/(t[1]−t[0]), v[2]=1/(t[2]−t[1]), . . . .

The intermittent continuous inputs are assumed inputs of which the continuous inputs of which the value of input speeds of each input v[1] to v[4] is high and the variation of these input speeds is small, such as i[1] to i[4], and an input after the continuous inputs are interrupted, of which the input speed v[5] is low to a certain extent such as i[5], are repeated in order, for example. Here, the continuous input number such as i[1] to i[4] is referred to as a continuous input number ni, the speed while the continuous inputs continue such as t[0] to t[4] is referred to as a continuous input speed vc, and the speed such as v[5] while the input is interrupted is referred to as a blank speed vb. Here, vc[1]=1/(t[4]−t[0]), vb[1]=v [5] is calculated.

In this case, in the primary display control information calculating unit 20, each of the continuous input speed vc, the blank speed vb, or the continuous input number ni can be used as the primary display control information. In addition, as information used for calculation of the primary display control information calculating unit 20, the information is not necessarily the input time of the each input at the input unit 320 of the user terminal 300 and may be input receiving time or the input number per unit time in the input receiving unit, for example. In a case of using the input number per unit time, S104 is performed at a time interval fixed in advance. The primary display control information which is calculated at S104 is the input number per unit time.

Figure 4:
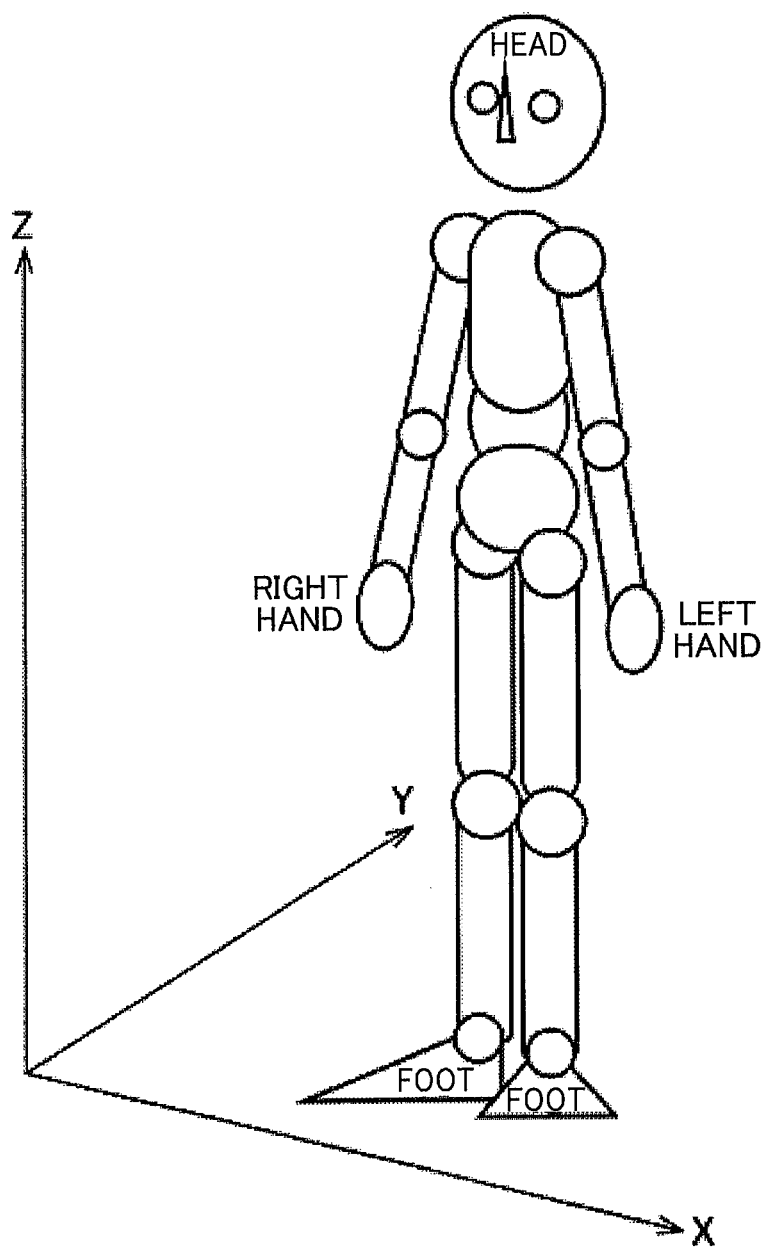
FIG. 4 is a view illustrating a coordinate system of an imaging target body.

Here, in FIG. 4, a coordinate system of a three-dimensional coordinate using in the following examples is illustrated. The volume data used in the examples sets each axis corresponding to a human body which is imaged since it is assumed that the volume data is obtained by imaging the human body. Here, in a state where a subject has arms put down, faces forward and stands upright, a direction from the right hand to the left hand is referred to as an X-axis, a direction from front to back is referred to as a Y-axis and a direction from the foot to the head is referred to as a Z-axis.

EXAMPLE 2

The secondary display control information calculated in the secondary display control information calculating unit 30 includes a section position in a case where the two-dimensional section image is generated from the volume data, a viewpoint position in a case where the three-dimensional visualization image is generated, or a three-dimensional reconfiguration resolution in a case where the three-dimensional visualization image is generated, or the like, for example, in addition to the display speed in a case where the two-dimensional section image or the three-dimensional visualization image are displayed.

In this example, in a case where the two-dimensional image generated in the image generation and transmission unit 40 is a continuous sectional view of a case where the volume data is cut in a plurality of parallel planes which are perpendicular to certain axis and are continuous on the axis, as an example of the secondary display control information determined according to the primary display control information, the time interval (display delay time) between the input times of inputs and the display time of the two-dimensional image is included. Hereinafter, a method for determining the time interval will be described.

Here, the continuous section is a plane which is perpendicular to the Z-axis and a Z coordinate thereof is s_0, s_1, . . . s-e. Here, s_0 and s_e indicate the section positions of both ends of the continuous two-dimensional section image which is generated from the three-dimensional volume data. In addition, the interval of each plane is a fixed value dis. The two-dimensional section image is reconstructed in advance as image [s_0] to image [s_e] so that one image corresponds to each section position, and is stored in the image data storage server 200.

In addition, as the interest region information, information on which the degree of interest is uniquely determined with respect to the section position in advance is stored in the image data storage server 200. Here, as an example thereof, the interest degree setting table is illustrated in FIG. 5. In FIG. 5, d_b is a higher value than d_a. In other words, FIG. 5 illustrates a case where the interest region between the section position s_r0 and the section position s_r1 is included.

In addition, here, one of the primary display control information is the input speed v which is calculated from information of the input and the secondary display control information calculating unit 30 uses a change flag f as one of the primary display control information. The change flag f indicates change history of the primary display control information and here while displaying an inside of the interest region having the same degrees of interest, the flag counts the number of times of the input speed v falling below a threshold v_th. Here, the threshold v_th is to detect the change of the input speed. Accordingly, v_th is determined according to the input speed so far, and for example, the previous input speed is v_th or an average of the input speed until the previous input is v_th.

The display control information storage unit 60 holds information in which the time interval between the input time and the display time is uniquely determined by the degree of interest, the input speed v which is the primary display control information, and the change flag f, in advance. A time interval setting table which is an example of the information is illustrated in FIG. 6. A case where ti_a is very small value and ti_b is a value which is greater than ti_a to the extent that a difference between the display speeds due to the difference between the time intervals can be visually recognized is illustrated in FIG. 6.

In a case where the degree of interest is d_b, the input speed v is equal to or greater than v_th, and f is less than f_th, the interval between the input time and the output time is increased to ti_b, and in a case of combinations in addition to this, the interval between the input time and the output time is decreased, as illustrated in FIG. 6. However, in a case where the change flag f is equal to or greater than the predetermined threshold f_th, that is, in a case where the number of times of the input speed v being less than v_th in the interest region is equal to or greater than f_th, the time interval is decreased to a fixed value ti_a, even in any case of FIG. 6.

A flow of a specific processing will be described. First, an image image[s[n]] is displayed in the image display unit 310 of the user terminal 300, and the input receiving unit 10 is in a state where i[n+1] which is one of the continuous inputs is received. As information corresponding to inputs i[0], . . . i[n] which is received so far at this point in time, a time t[0], . . . t[n] is stored in the input storage unit 50, and as the secondary display control information corresponding to the previous input i[n], the section position of display two-dimensional image s[n], and the time interval ti[n] are stored in the display control information storage unit 60.

The input receiving unit 10 receives the input time t[n+1] of the current input from the input unit 320 of the user terminal 300 and stores t[n+1] in the input storage unit 50. Next, the primary display control information calculating unit calculates the input speed v[n+1]=1/(t[n+1]−t[n]) calculated from t[n+1] and the previous input time t[n] and then stores the value in the display control information storage unit 60. The secondary display control information calculating unit 30 determines the time interval ti[n+1] from the current input speed v[n+1] and the history obtained from the display control information storage unit 60 and the interest region information obtained from the image data storage server 200.

Here, an example of algorithm of determining the time interval ti[n+1] by the secondary display control information calculating unit 30 will be described below. The previous section position s[n] is acquired and the next section position s[n+1] is obtained, from the display control information storage unit 60. Here, the section interval has a fixed value dis and is s[n+1]=s[n]+dis.

The secondary display control information calculating unit 30 refers to the interest degree setting table as illustrated in FIG. 5 and the degree of interest d[n+1] corresponding to the section position s[n+1] is obtained. At this time, in a case where d[n+1] is a value which is different from the degree of interest d[n] corresponding to the section position s[n], the change flag f is initialized to 0.

Next, the secondary display control information calculating unit 30 refers to the time interval setting table as illustrated in FIG. 6, the time interval ti[n+1] herein is obtained from the change flag f, the degree of interest d[n+1], and the input speed v[n+1], and the current section position s[n+1] is stored to the display control information storage unit 60. At this time, in a case where the input speed v[n+1] falls below v_th, the change flag f becomes f+1.

The image generation and transmission unit 40 acquires the two-dimensional image image[s[n+1]] corresponding to the section position s[n+1] from the image data storage server 200 and then transmits the acquired two-dimensional image image [s[n+1]] to the user terminal 300 and the two-dimensional image image[s[n+1]] is displayed on the input unit 320 from the input time after the time interval ti[n+1].

Here, a situation in which the interest region is presented by automatically changing the time interval from ti_a to ti_b, and an interactive operation is performed will be described. As an example, a case where the input of the continuous control signals of input i[0] to i[5] is provided and the section positions s[0] to s[5] corresponding to each control signal are provided will be described. Here, in a case where s[0] and s[1] are less than s_r0, s[5] is greater than s_r1, and s[2], s[3], and s[4] are equal to or greater than s_r0 and are less than s_r1, that is, s[2] to s[4] are inside the interest region and s[0], s[1], and s[5] are outside the interest region.

Figure 8:
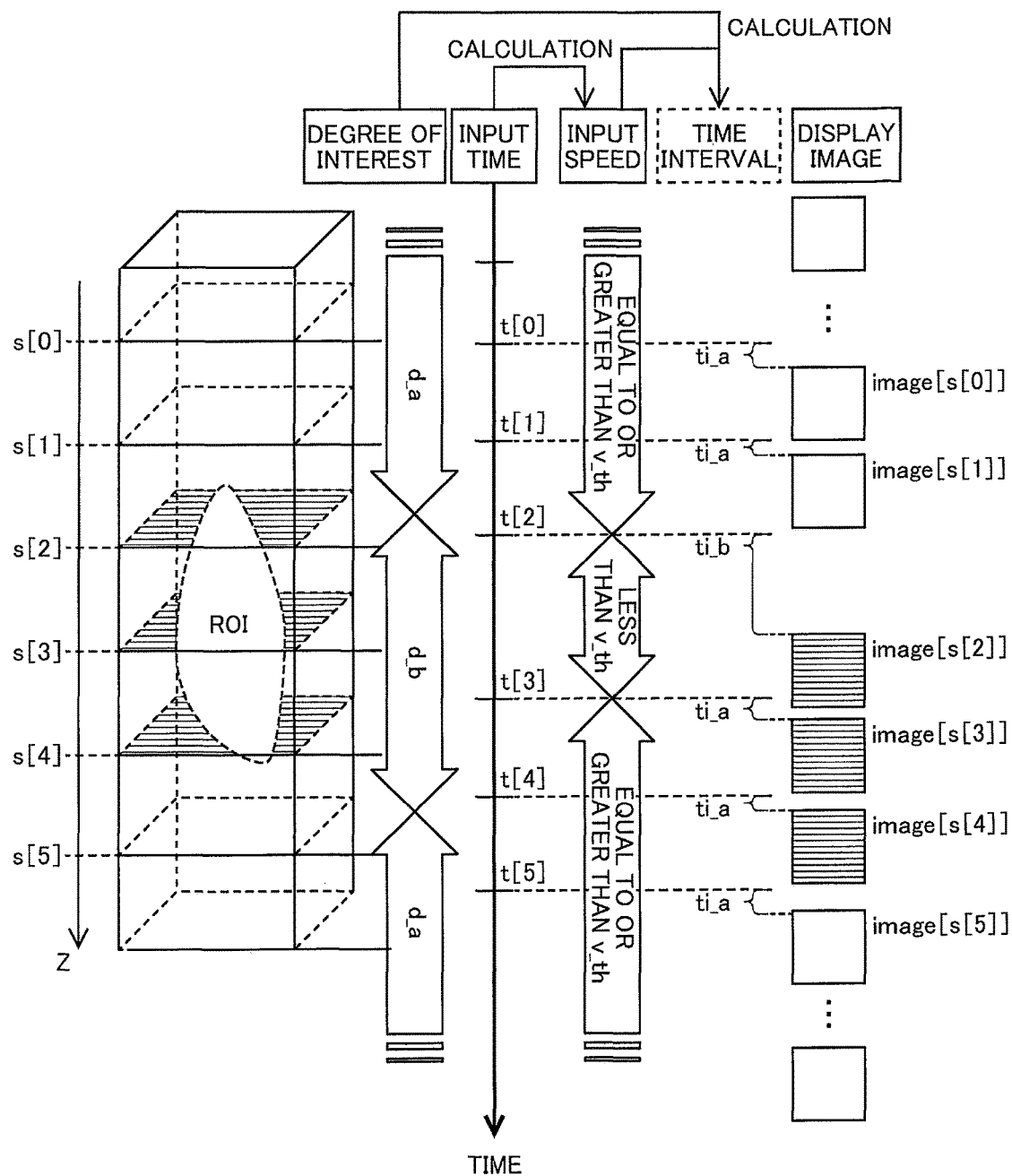
FIG. 8 is a view illustrating images which display two-dimensional image display timing, in a case where the time intervals from input to display are changed.

In this case, an example of a parameter change of a case where the input speeds v[0] to v[2] are equal to or greater than v_th, v[3] is less than v_th, and the change flag threshold f_th is 1 is illustrated in FIG. 7. In addition, an image of an image display timing corresponding to the change of the parameter is illustrated in FIG. 8.

Here, since a level of interest is displayed as d_a, that is, a region with low interest until the input i[0] to i[1], the time difference ti between the input time and the output time becomes a very small value as ti_a and the display is performed in the form of following-up the continuous inputs. Here, a case where the section position has entered the interest region is considered. Here, the threshold v_th is slightly smaller value than an average value of the input speed in a case of viewing regions other than the interest region (for example, a value of about 90% of the input speed average value when viewing the outside of the interest region). At the point in time of i[2], in a case where the input is performed with the same degree of the input speed as i[0] and i[1], since the input speed v[2] is equal to or greater than v_th, the time difference ti between the input time and the output time is increased to ti_b, and followability with respect to the continuous inputs is automatically decreased. Therefore, it is possible to draw the attention of the user in the case of entering the interest region.

Here, at the point in time of input i[3], in a case where a user delays the input speed, the input speed v[3] is less than v_th, the time interval returns from ti_b to ti_a, and returns to normal followability. Here, as described above, since v[2] is greater than v_th, the change flag f becomes 1 and thus equals to f_th, until the next display of the interest region is performed and the change flag f is initialized to 0, the followability is not reduced. This indicates that a scroll display of high followability becomes possible again because the user notices that the section position of the current display two-dimensional image is in the interest region due to the low follow-up with respect to the continuous inputs, and delays an operation controlling a display timing of the continuous two-dimensional image and thus ti is decreased from ti_b to ti_a.

In addition, here, a case where the present technique is used for a clinician to reduce the image interpretation time and decrease detection omission at a situation in which the image interpretation is performed while referring to the interest region set in the CAD system, will be explained.

The interest region information set by the CAD or the like is not always just enough information necessary for the user. In other words, in a case where a function detecting the disease suspicion region is used, there is a possibility that detecting of the disease region is failed or a region which is not clinically the disease region is detected according to a detection accuracy thereof. As a specific example of detecting a region which is not clinically the disease region, for example, there is a case where a treatment mark which is made by treatment in the past or a region where inflammation occurred, but not became a disease is detected as the disease suspicion site.

Here, assuming the mouse as the input unit 320 of the user terminal 300, there is a case where scrolling is performed by rotating the wheel thereof and thus the image interpretation is performed by sequentially viewing the continuous two-dimensional image which is generated from the three-dimensional image.

If a technique according to the present invention is used, at the time of approaching the disease areas that the display two-dimensional image is automatically detected, the following-up with respect to the scrolling operation is automatically reduced, and the approach to an automatically detected region can be presented by only with the two-dimensional image display region without displaying a thumb nail image or the like on another region. Here, in a case where the doctor notices the automatically detected region is displayed, the followability with respect to the scrolling operation returns to the original followability, by slowing the operation speed of the scroll than before.

In a case where the approach to the automatically detected region is noticed by doctor, it is not necessary to perform automatic presentation by the system thereafter. As a result of the automatically detected region being confirmed by eyes of the doctor, in a case where it is not a disease suspicion site, a high-speed display is required, and in a case where it is the disease suspicion site, a low-speed display is required. The operation thereof can be realized by following the scrolling operation speed of the doctor.

Therefore, high speed image interpretation without stress is possible, by determining whether or not the approach to the automatically detected region is noticed by doctor by a change of the scrolling operation speed and returning to the original followability of the scrolling operation speed.

EXAMPLE 3

In the present example, in the configuration of the image processing system illustrated in FIG. 1 and the flow illustrated in FIG. 2, a case of modifying the section interval of the two-dimensional section image which is reconstructed from the volume data in the secondary display control information determined according to the primary display control information will be described. In addition, here, in the same manner as in Example 2, as the primary display control information, the input speed v calculated from the input information is used, and the secondary display control information calculating unit 30 also holds the change flag f which counts the number of times of the input speed v falling below the threshold v_th as one of the primary display control information, while displaying the inside of the interest region having the same degree of interest.

Here, the display control information storage unit 60 holds in advance the information on which the section interval is uniquely determined from the degree of interest, the input speed, and the change flag. As an example of this information, the section interval setting table is illustrated in FIG. 9.

Hereinafter, the flow of the specific processing will be described. The image image [s[n]] is displayed in the image display unit 310 of the user terminal 300 and the process starts from a state where it is determined that the input receiving unit 10 has received the continuous inputs. At this point in time, as the previous information, the input times t[0], . . . t[n] are stored in the input storage unit 50 and the section position s[n] and the change flag f=0 are stored in the display control information storage unit 60.

The input receiving unit 10 stores the input time t[n+1] of inputs which are input from the input unit 320 of the user terminal 300 in the input storage unit 50. The primary display control information calculating unit 20 calculates the input speed v [n+1] and then stores a calculated input speed in the display control information storage unit 60. The secondary display control information calculating unit 30 determines the section position s[n+1] from the current input speed v [n+1] obtained from the display control information storage unit 60, the interest region information obtained from the image data storage server 200, and the section position s[n] of the previous two-dimensional display image and the change flag f obtained from the display control information storage unit 60.

Here, an example of an algorithm in which the secondary display control information calculating unit 30 determines the section position s[n+1] will be described.

The previous section position s[n] is acquired from the display control information storage unit 60, and s[n]+gm is obtained using a predetermined minimum section interval gm. As the interest region information, information on which the degree of interest is uniquely determined with respect to the section position is stored in advance in the image data storage server 200. The interest degree setting table as illustrated in FIG. 6 as an example is referred and in the calculation of the secondary display control information calculating unit 30, the degree of interest corresponding to the section position s[n]+gm becomes d[n+1].

Next, the secondary display control information calculating unit 30 refers to the section interval setting table (FIG. 9) stored in the image data storage server 200, determines the section interval g[n+1] from the degree of interest d[n+1] and the input speed v[n+1] and s[n+1]=s[n]+g[n+1] is obtained. Here, the secondary display control information calculating unit 30 again refers to the interest degree setting table of FIG. 5 and obtains the degree of interest d[n+1] corresponding to s[n+1].

Here, in a case where d[n+1] is a value which is different from the degree of interest d[n] corresponding to the section position s[n], the change flag f is initialized to 0. In a case where d[n+1] and d[n] are the same as each other and in a case where the input speed v[n+1] falls below v_th, the change flag f becomes f+1.

The image generation and transmission unit 40 generates the two-dimensional image image [n+1] corresponding to the section position s[n+1] from the volume data which is stored in the image data storage server 200, transmits the generated two-dimensional image to the user terminal 300, allows the image display unit 310 to display image [s[n+1]] after the time interval ti from the input time t[n+1], and stores the current section position s[n+1] in the display control information storage unit 60.

For example, in a case where s[n] is less than s_r0 and s[n]+gm is equal to or greater than s_r0 and is less than s_r1, the degree of interest is d_b in s[n+1] and the degree of interest is d_a in s[n], as can be seen from FIG. 5. Therefore, when d_b>d_a is considered, once reached s[n+1] from the s[n], the degree of interest is increased from d_a to d_b, and if v which is equal to or greater than v_th is considered when f is 0, the section interval is changed from g_a to g_b, as can be seen from FIG. 9. Here, for example, in a case where the value of g_b is set to be smaller than that of g_a, the two-dimensional image of which the section interval is narrower, that is, the two-dimensional section image of which the resolution between sections is high is displayed with respect to s[n+1] in which the degree of interest is high and thus it is possible to prompt the attention of the user.

EXAMPLE 4

In the present example, in the configuration and the flow described in Example 1, a case where the image generation and transmission unit 40 generates the three-dimensional visualization image will be described.

Assuming a plurality of parallel rays passing through the inside of the volume data, the three-dimensional visualization image is the two-dimensional image which processes and generates a voxel value according to certain law along the ray. As representative means for creating the three-dimensional visualization image, there are a surface rendering which views a surface of a voxel group having brightness which is equal to or greater than a fixed threshold in voxels of the volume data, a volume rendering which expresses also an inside of an object by setting opacity from the brightness value of the voxel of the inside of the volume data and overlapping the value thereof along the ray, an MIP rendering only the maximum brightness by the voxel present on the ray, or the like.

Here, a case where the interest degree information is set by the viewpoint angle will be described. The viewpoint angle will be explained below using FIG. 10.

Certain initial point p_(x_p0, y_p0, z_p0) is set first. In a case where a center of the volume data is v-c (x_pc, y_pc, z_pc), in a plane plane c perpendicular to the Z-axis through v_c, a point which intersects with Z-axis is p_c. p_c can be expressed as a three-dimensional coordinate (x_p0, y_p0, z_pc). Each point p_q on a circumference of a circle which is obtained by rotating a line segment 1_0 connecting p_c and the center v_c of the volume data with each other on the plane_c around v_c is a viewpoint position when generating the volume rendering. At this time, an angle between a line segment 1_q connecting p_q and v_c with each other and the line segment 1_0 is a viewpoint angle a_q.

Figures 10, 11:
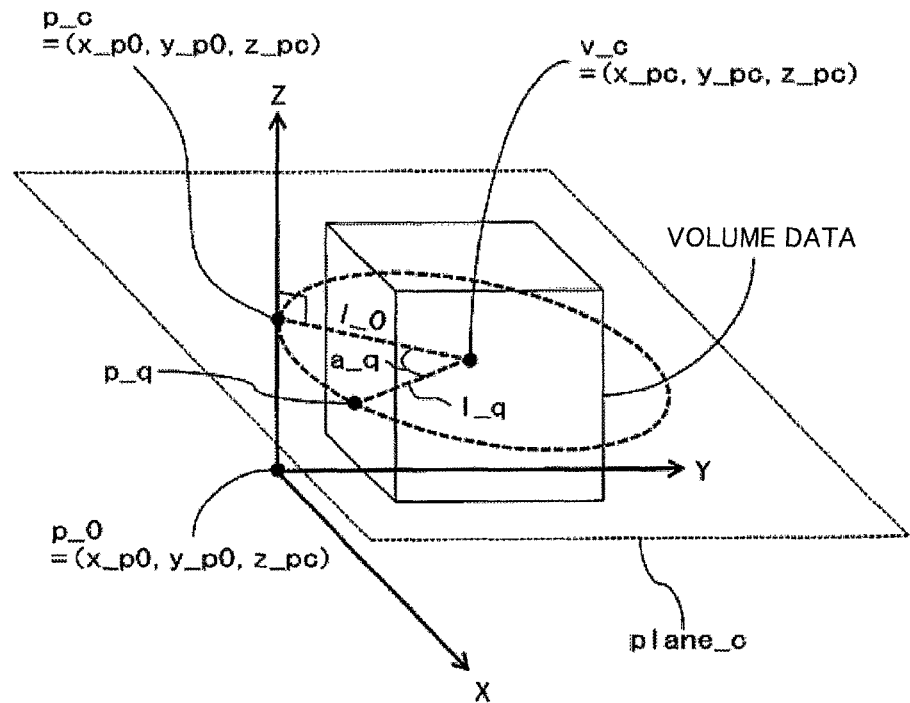
FIG. 10 is a view explaining a viewpoint angle and a viewpoint position using a three-dimensional coordinate system when creating a three-dimensional visualization image of volume data, according to Example 4.
FIG. 11 is a view illustrating the interest degree setting table in which the degree of interest with respect to the viewpoint angle when creating the three-dimensional visualization image is set.

The interest degree setting table of a case where the degree of interest is set by the viewpoint angle a_q is illustrated in FIG. 11. In this case, the two-dimensional image stored in the image data storage server 200 or the two-dimensional image generated in the image generation and transmission unit 40 are three-dimensional visualization images image[p_0] to image[p_2π] viewed from each viewpoint position p_q of a case a_q=0 to 2π.

As an example of the secondary display control information determined according to the primary display control information of a case where the three-dimensional visualization image becomes the two-dimensional image at the time of the output, in the same manner as in Example 1, the viewpoint angle, or the time interval between the input time and the display time of a case where the reconstructed three-dimensional visualization image is displayed, or ray density or a sampling interval on the ray when the three-dimensional visualization image is reconstructed can be used. The displayed three-dimensional visualization image image [p_0] to image [p_2π] may be created in advance and stored in the image data storage server 200 as described herein or it is also possible to create the image each time in the image generation and transmission unit 40.

In the Examples so far, as the information which indicates the interest region, as illustrated in FIG. 5, even if the interest degree setting table is described as an example in which the degree of interest with respect to the two-dimensional image section position is uniquely determined, the information which indicates the interest region is not only the two-dimensional image section position and the degree of interest with respect to the three-dimensional position can be set as the information, for example. As an example thereof, the interest degree setting table is described in FIG. 12. Three interest regions are indicated in the example of FIG. 12, the three-dimensional coordinates (x_r0, y_r0, z_r0), (x_r1, y_r1, z_r1), and (x_r2, y_r2, z_r2) indicate the center positions of the interest regions, respectively and r_r0, r_r1, and r_r2 indicate radiuses of each interest region.

Here, the interest region is a spherical shape and with respect to the regions of three inside portions of a sphere expressed from a center and a radius of the sphere, the degrees of interest are d_0, d_1, and d_2, respectively and with respect to the regions of three outside portions of the sphere, the degree of interest is d_3.

The present invention is not limited to the above examples and includes various modified examples. For example, the examples described above are described in detail in order to make the present invention easy to understand, and are not intended to be limited to be necessarily provided with all the configurations described. In addition, it is possible to replace a portion of the configuration of some example with the configuration of another example and in addition, it is possible to add the configuration of another example to the configuration of some example. In addition, with respect to a portion of the configuration of each example, it is possible to add, remove, and replace another configuration.

In Example 1, the image data storage server 200 is configured to be installed on the outside portion of the image processing device 100. However, the data stored in the image data storage server 200 may be configured to be stored in an inside storage device of the image processing device 100 or a storage unit of the image processing device 100 may be configured with the data stored (in the image data storage server 200 and data stored) in the storage unit of image processing device 100.

In addition, the user terminal 300 is configured to be connected to the image processing device 100 through the network 400. However, the user terminal 300 maybe configured to be directly connected to the image processing device 100.

REFERENCE SIGNS LIST

10: input receiving unit
20: primary display control information calculating unit
30: secondary display control information calculating unit
40: image generation and transmission unit
50: input storage unit 60: display control information storage unit
100: image processing device
200: image data storage server
300: user terminal

The invention claimed is:
1. An image processing system, comprising:
a storage server configured to store a three-dimensional image and a predetermined interest region in the three-dimensional image;
a user terminal configured to receive a plurality of input signals according to operation of an input device; and
an image processing device connected to the storage server and the user terminal, and configured to sequentially generate a plurality of two-dimensional section images from the three-dimensional image and cause the two-dimensional section images to be displayed at the user terminal,
wherein the image processing device is further configured to:
calculate primary display control information including an input speed of the received input signals,
calculate secondary display control information including a time interval based on the calculated primary display control information including the input speed, and
cause the two-dimensional section images to be sequentially displayed at the user terminal based on the calculated secondary display control information including the time interval,
wherein the image processing device is further configured to:
determine that the interest region is included in a currently displayed two-dimensional section image,
determine a change flag which is a number of times the input speed falls below a first threshold value,
when the interest region is included in a currently generated two-dimensional section image, when the input speed is greater than the threshold value and when the change flag is less than a second threshold value, increase the time interval by a predetermined amount from a first value to a second value, and
wherein the currently generated two-dimensional section image is caused to be displayed at the user terminal based on the calculated secondary display control information including the increased time interval.

2. The image processing system according to claim 1, wherein the interest region represents a disease suspicion site in an imaging region corresponding to the three-dimensional image.

3. The image processing system according to claim 1, wherein the primary display control information includes information representing intervals between continuous input signals from the user terminal.

4. The image processing system according to claim 1, wherein the primary display control information includes a number of the received input signals per unit time.

5. The image processing system according to claim 1, wherein the image processing device is further configured to:
when the interest region is not included in the currently generated two-dimensional section image, when the input speed is greater than the threshold value or when the change flag is less than the second threshold value, set the time interval to the first value.

6. The image processing system according to claim 1, wherein the image processing device is further configured to:
generate the two-dimensional section images in a plurality of parallel planes along an axis, and
when the interest region is included in the currently generated two-dimensional section image, when the input speed is greater than the threshold value and when the change flag is less than the second threshold value, decrease a distance interval along the axis from the currently generated two-dimensional section image to a next generated two-dimensional section image.

7. The image processing system according to claim 1, wherein the image processing device is further configured to:
generate the two-dimensional section images as three-dimensional visualization images which correspond to states where the three-dimensional image is viewed from a plurality of viewpoints in three dimensions, and
when the interest region is included in the currently generated two-dimensional section image, when the input speed is greater than the threshold value and when the change flag is less than the second threshold value, decrease an angle interval between the viewpoints from the currently generated two-dimensional section image to a next generated two-dimensional section image.

8. An image processing device connected to a user terminal, comprising:
a storage unit configured to store a three-dimensional image and a predetermined interest region in the three-dimensional image; and
a processor configured to:
receive a plurality of input signals according to operation of an input device of the user terminal, and
sequentially generate a plurality of two-dimensional section images from the three-dimensional image and cause the two-dimensional section images to be displayed at the user terminal,
wherein the processor is further configured to:
calculate primary display control information including an input speed of the received input signals;
calculate secondary display control information including a time interval based on the calculated primary display control information including the input speed, and
cause the two-dimensional section images to be sequentially displayed at the user terminal based on the calculated secondary display control information including the time interval,
wherein the processor is further configured to:
determine that the interest region is included in a currently generated two-dimensional section image,
determine a change flag which is a number of times the input speed falls below a first threshold value,
when the interest region is included in the currently generated two-dimensional section image, when the input speed is greater than the threshold value and when the change flag is less than a second threshold value, increase the time interval by a predetermined amount from a first value to a second value, and
wherein the currently generated two-dimensional section image is displayed at the user terminal based on the calculated secondary display control information including the increased time interval.

9. The image processing device according to claim 8, wherein the primary display control information includes information representing intervals between continuous input signals from the user terminal.

10. The image processing device according to claim 8, wherein the primary display control information includes a number of the received input signals per unit time.

11. The image processing device according to claim 8, wherein the processor is further configured to:

when the interest region is not included in the currently generated two-dimensional section image, when the input speed is greater than the threshold value or when the change flag is less than the second threshold value, set the time interval to the first value.

12. The image processing system according to claim 8, wherein the processor is further configured to:

generate the two-dimensional section images in a plurality of parallel planes along an axis, and when the interest region is included in the currently generated two-dimensional section image, when the input speed is greater than the threshold value and when the change flag is less than the second threshold value, decrease a distance interval along the axis from the currently generated two-dimensional section image to a next generated two-dimensional section image.

13. The image processing device according to claim 8, wherein the processor is further configured to:

generate the two-dimensional section images as three-dimensional visualization images which correspond to states where the three-dimensional image is viewed from a plurality of viewpoints in three dimensions, and when the interest region is included in the currently generated two-dimensional section image, when the input speed is greater than the threshold value and when the change flag is less than the second threshold value, decrease an angle interval between the viewpoints from the currently generated two-dimensional section image to a next generated two-dimensional section image.

14. An image processing method, the method comprising:

receiving a plurality of input signals according to operation of an input device of a user terminal;

sequentially generating a plurality of two-dimensional section images from a three-dimensional image and a predetermined interest region in the three-dimensional image and causing the two-dimensional section images to be displayed at the user terminal, including:

calculating primary display control information including an input speed of the received input signals, calculating secondary display control information including a time interval based on the calculated primary display control information including the input speed, and causing the two-dimensional section images to be sequentially displayed at the user terminal based on the calculated secondary display control information including the time interval, wherein the calculation of the secondary display control information includes:

determining that the interest region is included in a currently generated two-dimensional section image, determining a change flag which is a number of times the input speed falls below a first threshold value, when the interest region is included in the currently generated two-dimensional section image, when the input speed is greater than the threshold value and when the change flag is less than a second threshold value, increasing the time interval by a predetermined amount from a first value to a second value, and wherein the currently generated two-dimensional section image is displayed at the user terminal based on the calculated secondary display control information including the increased time interval.

\* \* \* \* \*